United States Patent [19]

Patel

[11] Patent Number: 4,755,176

[45] Date of Patent: Jul. 5, 1988

[54] CATHETER WITH SIDE HOLE

[76] Inventor: Piyush V. Patel, 2103 W. Michigan, Midland, Tex. 79701

[21] Appl. No.: 60,630

[22] Filed: Jun. 11, 1987

[51] Int. Cl.$^4$ .......................................... A61M 25/00
[52] U.S. Cl. ..................................... 604/280; 128/658
[58] Field of Search ..................................... 604/43–45, 604/51–53, 93, 95, 96, 103, 264, 280–283; 128/656–658

[56] References Cited

U.S. PATENT DOCUMENTS

| Re. 31,873 | 4/1985 | Howes ................................. 128/674 |
| 3,430,631 | 3/1969 | Abramson .......................... 604/282 |
| 4,117,836 | 10/1978 | Erikson .......................... 604/281 X |
| 4,129,129 | 12/1978 | Amrine ................................. 604/4 |
| 4,240,433 | 12/1980 | Bordow .............................. 604/158 |
| 4,423,725 | 1/1984 | Baran et al. ..................... 128/207.15 |
| 4,445,892 | 5/1984 | Hussein et al. ....................... 604/101 |
| 4,451,252 | 5/1984 | Martin ................................. 604/43 |
| 4,453,545 | 6/1984 | Inoue .............................. 120/207.15 |
| 4,568,329 | 2/1986 | Mahurkar ............................. 604/43 |
| 4,581,017 | 4/1986 | Sahota ............................ 604/102 X |
| 4,583,968 | 4/1986 | Mahurkar ............................. 604/43 |
| 4,610,662 | 9/1986 | Weikl et al. .................... 604/101 X |
| 4,655,746 | 4/1987 | Daniels et al. ......................... 604/53 |
| 4,689,041 | 8/1987 | Corday et al. ......................... 604/53 |

*Primary Examiner*—Dalton L. Truluck
*Attorney, Agent, or Firm*—Herbert J. Hammond

[57] ABSTRACT

A catheter for performing various medical procedures, such as coronary angiography or angioplasty. The catheter has an elongated, tubular, inner wall, enclosing a central lumen. An elongated, tubular, outer wall encloses the inner wall and a minor lumen between the inner and outer walls. A side hole passes through the outer wall, but not through the inner wall. Therefore, when the catheter is inserted into a coronary artery, blood can perfuse through the side hole and the minor lumen, without affecting the functions of the central lumen.

10 Claims, 1 Drawing Sheet

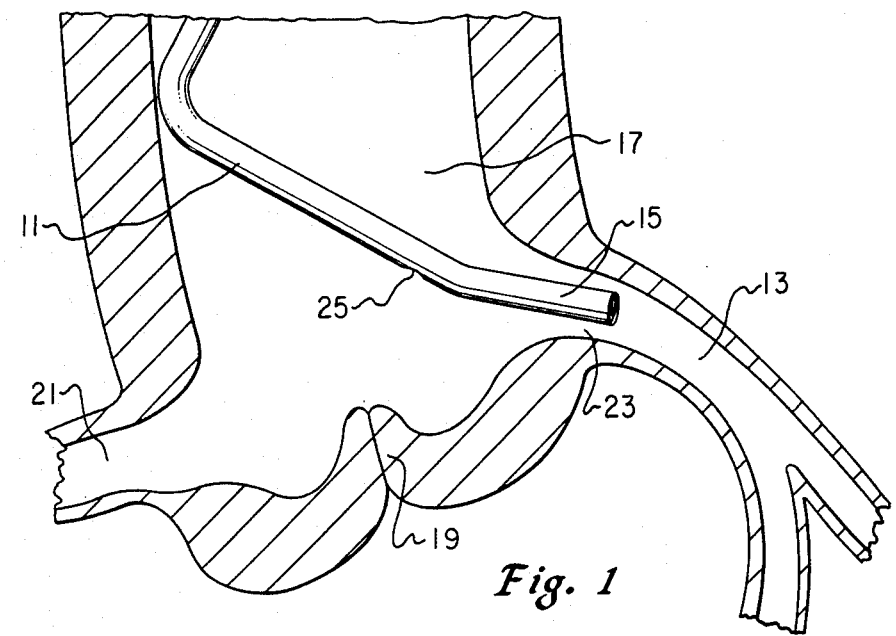
Fig. 1
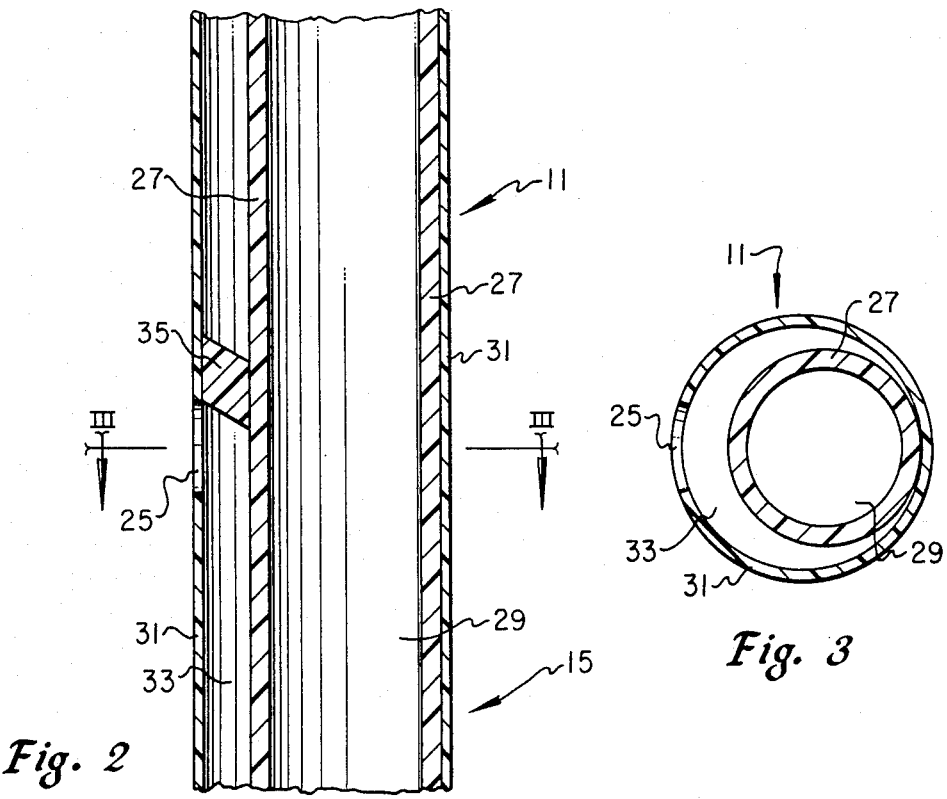
Fig. 2
Fig. 3

CATHETER WITH SIDE HOLE

BACKGROUND OF THE INVENTION

1. Field of the Invention

This invention relates in general to medical equipment and procedures. In particular, the invention relates to catheters for use in performing certain medical procedures, such as coronary angiography or angioplasty.

2. Description of the Prior Art

Coronary angiography and angioplasty involve the introduction of a catheter into the aorta, by way of the femoral artery, under local anesthesia. The distal end of the catheter is inserted into the opening of a selected coronary artery.

During such procedures, special precautions must be taken to prevent the catheter from blocking, or occluding, the opening of the coronary artery. Continuous blood flow must be maintained past the catheter into the artery. Blockage of the blood flow may cause ischemia, a localized tissue anemia due to the obstruction of the inflow of arterial blood. If dye is injected while the coronary artery is occluded, the result can be serious life threatening cardiac arrhythmia, such as ventricular tachycardia, ventricular fibrillation, cardiac arrest, or myocardial infarction.

One method of maintaining blood flow to the artery is by using a catheter with a hole through the side of the catheter. However, such a side hole has several disadvantages.

If there is a hole through the side of the catheter, the catheter cannot be used to monitor pressures at the distal opening of the catheter. The side hole communicates with the central lumen of the catheter, and interferes with the monitoring of the pressure at the distal end of the catheter.

The side hole in the catheter also prevents the use of the catheter to inject dye into the coronaries. If such a catheter is used to inject dye, most of the dye exits through the side hole, rather than through the distal end of the catheter.

DESCRIPTION OF THE DRAWINGS

FIG. 1 is a side view of a catheter of the invention, with the distal end of the catheter inserted into the opening of a coronary artery.

FIG. 2 is a sectional view of the catheter of the invention.

FIG. 3 is a cross-sectional view of the catheter of the invention, as seen along lines 3—3 in FIG. 2.

DESCRIPTION OF THE PREFERRED EMBODIMENT

FIG. 1 shows the catheter 11 of the invention, inserted into the opening of the left main coronary artery 13. The distal end 15 of the catheter 11 has been passed through the femoral artery to the aorta 17. FIG. 1 shows only a section of the aorta 17, the aortic valve 19, the right main coronary artery 21, and the left main coronary artery 13.

The catheter 11 is shown inserted into the opening, or ostium 23, of the left main coronary artery 13. Other catheters may be shaped differently, for insertion elsewhere, such as into the right main coronary artery 21 or into the aortic valve 19. The left coronary catheter 11, shown in FIG. 1, is shown merely as an example.

Blood normally flows from the heart through the aortic valve 19 intoo the aorta 17. The blook then flows into the various coronary arteries 13, 21. A catheter 11, inserted into the ostium 23 of an artery 13, may block the flow of blood into that artery 13.

The catheter 11 of the invention is designed to maintain the flow of blood into the coronary artery 13. The catheter 11 has a side hole 25, through which blood can flow. However, because of the structure of the catheter 11, the side hole 25 does not interfere with the functions of the catheter 11.

FIGS. 2 and 3 show the structure of the catheter 11 in greater detail. The catheter 11 has an elongated, tubular, inner wall 27. This inner wall 27 encloses a central lumen 29.

The inner wall 27 and the central lumen 29 are enclosed within an elongated, tubular, outer wall 31. The outer wall 31 also encloses a minor lumen 33, which is located between the inner and outer walls 27, 31. The inner and outer walls 27, 31 both have circular cross sections, as shown in FIG. 3. The inner wall 27 is offset from the center of the outer wall 31, so the minor lumen 33 has a crescent shape.

The side hole 25 passes through the outer wall 31, but not through the inner wall 27. The inner wall 27 is solid, to segregate any fluids in the central lumen 29 from any fluids within the minor lumen 33.

There is a barrier 35 in the minor lumen 33 above the side hole 25. Therefore, any blood entering through the side hole 25 must flow toward the distal end 15 of the catheter 11 through the minor lumen 33.

The catheter 11 of the invention has several advantages over the prior art. The side hole 25 and the minor lumen 33 allow blood to perfuse past the catheter 11 into the artery 13. However, there is still a central lumen 29, which can be used to perform all of the well-known functions of a catheter. The side hole 25 does not diminish nor eliminate any of the normal functions of the catheter 11.

Only the preferred embodiment of the invention has been illustrated. It should be understood that the invention is not limited to the embodiment disclosed, but is capable of numerous rearrangements, modifications, and substitutions of parts and elements, without departing from the scope of the invention.

I claim:

1. A catheter comprising:
   an elongated, tubular, outer wall having a side hole;
   an inner wall, within the outer wall, defining a central lumen and a minor lumen between the inner and outer walls for carrying fluid between the side hole and the distal end of the catheter; and
   a barrier in the minor lumen between the inner and outer walls proximate to the side hole to direct the flow of fluid.

2. A catheter, as recited in claim 1, wherein the inner wall is solid to segregate fluids in the central lumen from fluids in the minor lumen.

3. A catheter, as recited in claim 1, wherein the central lumen has a circular cross section.

4. A catheter, as recited in claim 2, wherein the central lumen has a circular cross section.

5. A catheter comprising:
   an elongated, tubular, inner wall, enclosing a central lumen;
   an elongated, tubular, outer wall, having a side hole and enclosing the inner wall to form a minor lumen between the inner and outer walls for carrying fluid between the side hole and the distal end of the catheter; and a barrier in the minor lumen between the inner and outer walls proximate to the side hole to direct the flow of fluid.

6. A catheter, as recited in claim 5, wherein the inner wall is solid to segregate fluids in the central lumen from fluids in the minor lumen.

7. A catheter, as recited in claim 5, wherein the central lumen has a circular cross section.

8. A catheter, as recited in claim 6, wherein the central lumen has a circular cross section.

9. A catheter comprising:

an elongated, tubular, inner wall, enclosing a central lumen; and an elongated, tubular, outer wall, enclosing the inner wall to form a minor lumen between the inner and outer walls, the outer wall having a distal end for insertion through an aorta into an ostium of an artery, and the outer wall having a side hole spaced axially from the distal end to allow blood to flow from the aorta through the side hole and the minor lumen and out through the distal end of the outer wall the minor lumen having means located proximate the side hole for directing flow of fluid.

10. A catheter comprising an elongated, tubular, outer wall enclosing an elongated, tubular, inner wall, and having a distal end for insertion through an aorta into an ostium of an artery, the outer wall having a side hole spaced axially from the distal end positioned within the aorta when the distal end of the outer wall is in the ostium, and forming a minor lumen within the inner wall to carry fluid between the side hole and the distal end of the outer wall the minor lumen having means located proximate the side hole for directing flow of fluid.

* * * * *